US011672764B2

(12) United States Patent
Hoppu et al.

(10) Patent No.: US 11,672,764 B2
(45) Date of Patent: Jun. 13, 2023

(54) METHOD FOR COATING PHARMACEUTICAL SUBSTRATES

(71) Applicant: Applied Materials, Inc., Santa Clara, CA (US)

(72) Inventors: Pekka Hoppu, Kitee (FI); Tommi Kaariainen, Mikkeli (FI); Marja-Leena Kaariainen, Mikkeli (FI); Aimo Turunen, Kitee (FI)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 16/806,625

(22) Filed: Mar. 2, 2020

(65) Prior Publication Data

US 2020/0197313 A1 Jun. 25, 2020

Related U.S. Application Data

(60) Continuation of application No. 15/275,900, filed on Sep. 26, 2016, now Pat. No. 10,603,284, which is a division of application No. 14/428,530, filed as application No. PCT/FI2013/050896 on Sep. 17, 2013, now abandoned.

(30) Foreign Application Priority Data

Sep. 18, 2012 (FI) ...................................... 20125962

(51) Int. Cl.
| | | |
|---|---|---|
| A61K 9/00 | (2006.01) | |
| A61K 9/50 | (2006.01) | |
| C23C 16/40 | (2006.01) | |
| C23C 16/44 | (2006.01) | |
| A61K 9/20 | (2006.01) | |
| C23C 16/455 | (2006.01) | |
| A61K 31/167 | (2006.01) | |

(52) U.S. Cl.
CPC .......... *A61K 9/2095* (2013.01); *A61K 9/2009* (2013.01); *A61K 9/2018* (2013.01); *A61K 9/2077* (2013.01); *A61K 9/2081* (2013.01); *A61K 9/501* (2013.01); *A61K 9/5015* (2013.01); *A61K 31/167* (2013.01); *C23C 16/403* (2013.01); *C23C 16/405* (2013.01); *C23C 16/45525* (2013.01); *C23C 16/45555* (2013.01)

(58) Field of Classification Search
CPC .. A61K 31/167; A61K 9/2009; A61K 9/2018; A61K 9/2077; A61K 9/2095; A61K 9/501; A61K 9/5015; C23C 16/403; C23C 16/405; C23C 16/45555
See application file for complete search history.

(56) References Cited

U.S. PATENT DOCUMENTS

| | | |
|---|---|---|
| 4,289,871 A | 9/1981 | Rowan et al. |
| 6,165,512 A | 12/2000 | Mezaache et al. |
| 6,613,383 B1 | 9/2003 | George et al. |
| 7,357,910 B2 | 4/2008 | Phillips et al. |
| 8,524,772 B2 | 9/2013 | Arad et al. |
| 8,697,097 B2 | 4/2014 | Nonomura et al. |
| 10,166,198 B2 * | 1/2019 | Carlsson ............... A61K 9/5192 |
| 10,478,402 B2 * | 11/2019 | Carlsson ................ A61K 9/145 |
| 10,512,796 B2 | 12/2019 | Toledano et al. |
| 2003/0026989 A1 | 2/2003 | George et al. |
| 2003/0118642 A1 | 6/2003 | Norman et al. |
| 2005/0266078 A1 | 12/2005 | Jorda et al. |
| 2006/0263479 A1 | 11/2006 | Boghani et al. |
| 2007/0036850 A1 | 2/2007 | Roehrich et al. |
| 2007/0280895 A1 * | 12/2007 | Weimer ................... A61K 8/29 424/59 |
| 2009/0186968 A1 | 7/2009 | Zeng et al. |
| 2010/0136110 A1 | 6/2010 | Tasaki et al. |
| 2010/0297251 A1 | 11/2010 | Timmons et al. |
| 2010/0303722 A1 | 12/2010 | Jin et al. |
| 2011/0091563 A1 | 4/2011 | Kurasawa et al. |
| 2011/0300224 A1 | 12/2011 | Murpani et al. |
| 2012/0201860 A1 | 8/2012 | Weimer et al. |
| 2013/0202790 A1 | 8/2013 | Li et al. |
| 2017/0007545 A1 | 1/2017 | Hoppu et al. |
| 2019/0216742 A1 | 7/2019 | Neikirk et al. |

(Continued)

FOREIGN PATENT DOCUMENTS

| | | |
|---|---|---|
| DE | 10307568 | 9/2004 |
| EP | 1621187 | 2/2006 |
| IN | 802 | 2/2005 |

(Continued)

OTHER PUBLICATIONS

Singh et al. ( Res Pharm Sci. Jul.-Dec. 2010; 5(2): 65-77). (Year: 2010).*
Wu et al. (J Mater Sci 2006;41:5845-5850) (Year: 2006).*
Siddiqi et al. (Nanoscale Research Letters 2018;13:13 pages). (Year: 2018).*
Shah et al. (AAPS PharmSciTech 2008;9(1):250-258). (Year: 2008).*
Prescott et al. On Powder Flowability. Pharmaceutical Technology Oct. 2000; pp. 60-84; 14 pages). (Year: 2000).*

(Continued)

*Primary Examiner* — Ernst V Arnold
(74) *Attorney, Agent, or Firm* — Fish & Richardson P.C.

(57) ABSTRACT

The present invention relates to the field of coating pharmaceutical substrates. In particular, the invention relates to methods of coating of pharmaceutical substances, pharmaceutical ingredients or a blend of them. The invention also provides a method of making a pharmaceutical formulation which may be processed into a pharmaceutical dosage form, which utilizes solid pharmaceutical particles and a pharmaceutical formulation obtained by the method. The methods of the invention utilize atomic layer deposition technology. The novel methods allow difficult, moisture sensitive and electrically charged pharmaceutical substrates to be easily processable.

23 Claims, No Drawings

(56) References Cited

U.S. PATENT DOCUMENTS

| | | |
|---|---|---|
| 2022/0105048 A1 | 4/2022 | Wang et al. |
| 2022/0202732 A1 | 6/2022 | Neikirk et al. |

FOREIGN PATENT DOCUMENTS

| | | | |
|---|---|---|---|
| JP | 2004269384 | 9/2004 | |
| JP | 2005060309 | 3/2005 | |
| JP | 2005520796 | 7/2005 | |
| JP | 2008013480 | 1/2008 | |
| JP | 2008539801 | 11/2008 | |
| JP | 2010501538 | 1/2010 | |
| JP | 2011-063627 | 3/2011 | |
| JP | 2012051810 | 3/2012 | |
| JP | 2014510066 | 4/2014 | |
| JP | 2015-528487 | 9/2015 | |
| JP | 2016-519155 | 6/2016 | |
| KR | 10-20140011358 | 1/2014 | |
| KR | 10-20160013050 | 2/2016 | |
| KR | 10-2016-0090478 | 8/2016 | |
| KR | 10-20170094046 | 8/2017 | |
| WO | WO 90/02546 | 3/1990 | |
| WO | WO-2005044224 A2 * | 5/2005 | ....... A61K 47/48869 |
| WO | WO 2006/090640 | 8/2006 | |
| WO | WO 2007/015243 | 2/2007 | |
| WO | WO 2008/023184 | 2/2008 | |
| WO | WO 2010/135107 | 11/2010 | |
| WO | WO 2012/116814 | 9/2012 | |
| WO | WO 2019/143744 | 7/2019 | |

OTHER PUBLICATIONS

Titanium oxide ([online] retrieved on Aug. 20, 2021 from: https://en.wikipedia.org/wiki/Titanium_oxide; 1 page). (Year: 2021).*
Arin et al. (Res Chem Intermed 2017;43:3183-3195). (Year: 2017).*
Li et al. (Journal of Nanoscience and Nanotechnology 2006;6:3252-3260) (Year: 2006).*
Li, J., Hastings, G.W. (1998). Oxide bioceramics: inert ceramic materials in medicine and dentistry. In: Black, J., Hastings, G. (eds) Handbook of Biomaterial Properties. Springer, Boston, MA). 4 pages. (Year: 1998).*
Arya et al. Zirconia Biomaterials 2022; 4 pages). (Year: 2022).*
Mftah et al. (International Journal of Nanomedicine 2015:10 765-774) (Year: 2015).*
'www.ahdictionary.com' [online]. "granule," [retrieved on Aug. 9, 2019]. Retrieved from the Internet: <https:www.ahdictionary.com/word/search/html?q=granule>, 3 pages.
European Search Report dated May 31, 2016 issued in corresponding European Patent Application No. 13838806.1, 7 pages.
Finnish Search Report corresponding to Finnish Patent Appln. No. 20125962, dated Apr. 7, 2014.
International Preliminary Report on Patentability dated Jan. 15, 2015 issued in PCT/FI2013/050896, 9 pages.
International Search Report dated Dec. 19, 2013 issued in PCT/FI2013/050896.
JP Office Action in Japanese Application No. 2015-531616 dated Mar. 13, 2018.
JP Office Action in Japanese Application No. 2019-071781, dated Mar. 31, 2020, 8 pages (With English Translation).
Knez et al., "Atomic Layer Deposition on Biological Macromolecules: Metal Oxide Coating of Tobacco Mosaic Virus and Ferritin," Nano Letters, 2006, 6(6):1172-7.
Martino et al., "A new pure paracetamol for direct compression: The orthorhombic form," International Journal of Pharmaceutics, 1996, 128: 1-8.
Patel et al., "Ensuring Better Control of Granulation", Pharmaceutical Manufacturing, Aug. 7, 2008, http://www.pharmamanufacturing/com/articles/2008/096/, 11 pages.
Pharmaceutical Preparations European Pharmacopoeia 8.0, (Apr. 2013), pp. 756-758.
Verheezen et al., "Milling of agglomerates in an impact mill," Int. J Pharm. 2004, 278:165-172.
Xie el al. "Atomic layer deposition of TiO2 from tetrakis-dimethyl-amido titanium or Ti isopropoxide precursors and H2O," Journal of Applied Physics, 2007, 102:7 pages.
JP Office Action in Japanese Application No. 2019-071781, dated Dec. 1, 2020, 5 pages (with English translation).
Andrew et al., "Sustained Release of a Monoclonal Antibody from Electrochemically Prepared Mesoporous Silicon Oxide," Advanced Functional Materials, Dec. 2010, 20(23):4168-4174.
Arl et al., "SiO2 thin film growth through a pure atomic layer deposition technique at room temperature," Royal Society of Chemistry, May 2020, 10:18073-18081.
Klaus et al., "SiO2 Chemical Vapor Deposition at Room Temperature Using SiCl4 and H 2 O with an NH 3 Catalyst," Journal of the Electrochemical Society, 2000, 147(7):2658-2664.
Groner et al., "Low-temperature Al2O3 atomic layer deposition," Chemistry of Materials, Chemistry of Materials, American Chemical Society, US, Feb. 24, 2004, 16(4):639-645.
Kaariainen et al., "Surface modification of acetaminophen particles by atomic layer deposition," International Journal of Pharmaceutics, Apr. 18, 2017, 525(1):160-174.
Knez et al., "Synthesis and Surface Engineering of Complex Nanostructures by Atomic Layer Deposition," Advanced Materials, Nov. 5, 2007, 19(21):3425-3438.
Office Action in Japanese Appln. No. 2019-071781, dated Feb. 15, 2022, 22 pages (with partial English translation).
Hakim et al., "Conformal nanocoating of zirconia nanoparticles by atomic layer deposition in a fluidized bed reactor," Nanotechnology, 2005, 16:S375-S381.
Huo et al., "Pre-Treatment with Zirconia Nanoparticles Reduces Inflammation Induced by the Pathogenic H5N1 Influenza Virus," International Journal of Nanomedicine, 2020, 15:661-674.

* cited by examiner

METHOD FOR COATING PHARMACEUTICAL SUBSTRATES

CROSS REFERENCE TO RELATED APPLICATION

The present application is a continuation application of U.S. Ser. No. 15/275,900, filed Sep. 26, 2016, which is a continuation application of U.S. Ser. No. 14/428,530, filed Mar. 17, 2015, which is the National Phase of PCT/FI2013/050896 filed Sep. 17, 2013, which claims priority to Finnish Application No. 20125962, filed Sep. 18, 2012, the entire contents of which are incorporated herein by reference.

FIELD OF THE INVENTION

The present invention relates to the field of coating pharmaceutical substrates. In particular, the invention relates to a method of coating of pharmaceutical substrates and a method of making a pharmaceutical formulation.

BACKGROUND OF THE INVENTION

Many tablets today are coated after being pressed. Coating is used to surround or coat a pharmaceutically active ingredient or drug by at least one layer of a surface. Coating is used for recognition, for purposes of masking the taste, or for controlled release purposes to change dissolution properties of active agent. Coating can also been used to work as a barrier against atmospheric stress e.g. humidity, UV-light and oxygen to increase physical and chemical stability of the active agent.

Various methods of coating pharmaceuticals or medical devices are known. Modern tablet coatings are polymer and polysaccharide based, with plasticizers and pigments included. The tablet coating process is complex, and involves parameters such as the spray pattern, drop size, and nozzle spacing, in addition to multiple other non-spray related parameters which must all be precisely controlled in order to ensure uniform distribution of the coating material.

Prior art discloses several methods for coating or encapsulating pharmaceuticals. WO9002546 discloses microencapsulated pharmaceuticals, which are formed by vapor depositing a polymeric film around a core comprising an active pharmaceutical agent to provide effective controlled release activity. DE 10307568 discloses membranes useful in pharmaceutical industry, which have reduced diameter micro- or nanopores produced by coating film with etched or laser produced openings. US 2010/0297251 discloses a method of encapsulating an active pharmaceutical agent with a controlled release coating layer using a gas phase chemical vapor deposition process. The coating materials used are monomers or carbonaceous compounds that upon polymerization yield polymers or polymer films that are degradable or nondegradable. US2009/0186968 discloses atomic plasma deposited coatings over a drug attached to a porous metal substrate. The method is applicable on drugs attached or adhering to a stent surface.

Pharmaceutical industry has a great desire to reduce costs and find new approaches for drug manufacturing and drug delivery. Current approaches of preparing pharmaceutical formulations and pharmaceutical dosage forms are complex, involve a number of technical steps, require special additives or treatments and result in pharmaceutical products with poor stability. In addition, most methods result in low product yields, due, in part, to the limited tolerance of the starting materials to industrial operating conditions and the numerous technical difficulties associated with the coating process. Especially challenging is the dissolution and controlled delivery of poorly soluble pharmaceuticals. Undoubtedly, there is a need for more efficient methods which improve processing techniques and processability of drugs which have poor flow properties and lack of compressibility. Moreover, there remains a need of developing a robust process of preparing pharmaceutical formulations which can be directly processed into the final dosage forms.

BRIEF DESCRIPTION OF THE INVENTION

An object of the present invention is thus to provide a method so as to solve the above problems. In particular, the object of the present invention is to provide an advantageous method for coating pharmaceuticals, which improves processability of drugs having poor flow properties and lack of compressibility. In addition, the object of the present invention is to provide an effective method for making a pharmaceutical formulation.

The objects of the application are achieved by a method wherein a layer of protective material is applied on the surface of a pharmaceutical substrate using an ALD (Atomic Layer Deposition) method or other corresponding technology. The objects of the application are further achieved by a method of making a pharmaceutical formulation, wherein the pharmaceutical substrate is first coated by ALD, an optional mixture of the coated substrate and excipients is formed and thereafter processed into a desired dosage form in which solid pharmaceutical particles are utilized. The present invention also relates to a pharmaceutical formulation obtained by the method. Additionally, the objects of the application are achieved by a pharmaceutical formulation consisting of individual pharmaceutical particles wherein each individual particle comprises an active pharmaceutical agent and wherein each individual particle is coated by ALD method. The present invention also relates to the use of the ALD method or other corresponding technology for coating a pharmaceutical substrate.

The preferred embodiments of this invention are disclosed in the dependent claims.

The inventors of the present application surprisingly noticed that when coating of pharmaceutical substrates is performed before the processing into a solid dosage form a significant improvement in the manufacturing process of pharmaceutical formulations can be obtained. The ALD coating layer coats the individual pharmaceutical particles allowing obtaining dosage forms composed of coated individual particles, without any obligatory need to use excipients such as fillers, binders, disintegrants or lubricants. The properties of such a coated material are considerably better in the further processing of the pharmaceutical formulation into a suitable dosage form.

An advantage to the method of the invention is that difficult, moisture sensitive, electrically charged pharmaceutical substrates can be made more easily processable. The coating generated by the method is thin, dense and smooth; moreover the coating layers deposited by ALD are pinhole-free and very conformal. The pharmaceutical formulations obtained by the methods of the present invention are uniform in the content, which ensures that the same active pharmaceutical ingredient dose is delivered within each dosage form. In addition, the pharmaceutical formulations of the present invention have good protection against moisture, oxygen and light. Furthermore, poor drug solubility may be overcome with an individually tailored coating to allow for modified or sustained release in a specific environment. The consumption of the coating material is low, and thus coating costs may be reduced. In addition, the coated components reduce dosing and administration of associated agents or particles.

The thickness of the coating layer may be controlled by varying the number of molecule layers in the coating. The term thin layer means in this context a layer that may have any thickness between 1 nm and 500 μm, the thickness depends on the pharmaceutical agent, pharmaceutical ingredients and the desired final dosage form.

The coating process of the invention is not sensitive to minor changes in the process parameters, and thus the repeatability of the method is good. Such a uniform layer is not possible to be provided on a three dimensional object for example with CVD method (Chemical Vapor Deposition) or PVD (Physical Vapor Deposition) method, since the coating process may not be controlled in such a detail as with the ALD method. CVD and other similar methods also require that the coated object have to be rotated for providing coating material over the whole surface of the three dimensional object.

One of the advantages of present invention is the ability to individually coat particles on both the micro and nano scales. The processing of nanoparticles has been extremely laborious due to electricity, physical interactions and their natural tendency for aggregation.

Another advantage of the present invention is that the process is solvent free, which allows highly soluble as well as highly insoluble drug particles to be easily coated in dry form. The invention overcomes the difficulties of using standard wet chemistry techniques with aqueous solutions wherein highly soluble particles dissolve before they can be coated or the pharmaceutical ingredient or drug substance changes the polymorphic form during processing. Likewise the use of organic and sometimes toxic solvents and plasticizers to apply a coating is not required and hence the chance of incorporation of these undesirable compounds is eliminated.

DETAILED DESCRIPTION OF THE INVENTION

The present invention relates to a method, wherein pharmaceutical substrates are coated by Atomic Layer Deposition (ALD) or other corresponding technology before processing into a final dosage form in which solid pharmaceutical particles are utilized.

A pharmaceutical substrate to be coated in the present invention may be any active pharmaceutical substance, pharmaceutical ingredient, or a blend of them which is in a solid form and capable of being deposited without changing structure and losing efficacy. The pharmaceutical substrate may contain one or more active pharmaceutical substances or pharmaceutical ingredients. The substrate may be, for example, a particle, granule, pellet, tab let or powder. Preferably it is a particle. A pharmaceutical formulation is a medicinal composition, including the active pharmaceutical substance, administered in a specific dosage form.

The term "pharmaceutical", "pharmaceutical substance", "therapeutic agent" or "drug" as used herein, refers to a medicinally administered composition or compositions as a whole. The terms refers to the active medicament which has a therapeutic effect intended to cure, alleviate, treat or prevent a disease or a symptom or condition suffered by the patient.

The pharmaceutical substrate to be coated may also be a biomolecule, a small molecule, or cells. The biomolecules may be, for example, peptides, polypeptides, oligonucleotides; nucleic acids and genes. The small molecules may be, for example, nucleotides, amino acids, sugars, carbohydrates, lipids and compounds which have a molecular weight of less than 100 kD.

Atomic layer deposition (ALD) is a generally known coating method in which surfaces of a substrate are subjected to alternating surface reactions of at least a first and second gaseous precursor. One ALD-cycle is completed when the surfaces of the substrate are subjected once to both or all gaseous precursors. Each time the surface of the substrate is subjected to a precursor, a monolayer of material is formed on the surfaces of the substrate. These ALD-surface reactions are normally substantially saturated surface reactions, meaning that the only one monolayer of material is formed on the surfaces of the substrate when the substrate is subjected to a precursor. One basic characteristic of ALD method is the conformability of the surfaces reactions. This means that the ALD growth layers of material grow on all the surfaces which are subjected to the precursors. Thus the coating is formed on all surfaces. In the present context the term atomic layer deposition covers also atomic layer epitaxy (ALE) and other corresponding coating methods in which the material growth is based on successive substantially self-limiting surface reactions of at least two gaseous precursors.

One corresponding coating method is molecular layer deposition (MLD). MLD is also based on sequential, self-limiting surface reactions. However, a "molecular" fragment, which is organic and can contain inorganic constituents, is deposited during MLD. The deposition of purely organic polymer MLD films can be achieved using step-wise condensation reactions. Hybrid organic-inorganic films can be deposited by simply mixing organic and inorganic reactants.

Only one atomic layer is produced on the surface of the substrate during one ALD cycle. This self-controlled growth mode contributes several advantages. The thickness of the films can be controlled in a straightforward manner by controlling the number of reaction cycles, therefore enabling the controlled growth of sub-nanometer thin layers. The precursors form stoichiometric films with large area uniformity and conformity even on complex surfaces with deformities and on particles. Layer-by-layer growth allows one to change the material abruptly after each step. This gives the possibility of depositing multicomponent films, so called nanolaminates or mixed oxides. It is also possible to develop the dissolution characteristics.

In the present application pharmaceutical particle formulations are loaded into the ALD reactor and pumped down to the operating pressure of around 2 mbar. The ALD precursors are introduced into the reactor from the inlet port after which they are forced to travel through all the cells before exhausted from the exhaust port connected to the uppermost cell. During this process the desired precursor chemicals will be diffused into the matter on the cell and consequently react with its active surface groups forming a chemical bonding between the substrate surface and precursor molecule. In the present invention the substrate to be coated is the individual particle within the pharmaceutical formulation. While the coating will be formed on the surface with molecular layer accuracy the bulk properties of particle will not be changed.

In one embodiment of the present application, paracetamol is coated with one or more molecule layers of aluminum oxide $Al_2O_3$. Trimethyl aluminum $(CH_3)_3Al$ is used as a precursor and water $H_2O$ as an oxygen source. In the present invention also other compounds, such as hydrogen peroxide $H_2O_2$ or ozone $O_3$ may be used as the oxygen source instead of water.

In other embodiment of the present invention, a pharmaceutical substrate is coated with titanium dioxide ($TiO_2$). An advantage of selecting titanium as a coating layer is titanium's well known compatibility in vivo and its track record of use in medical implants. Titanium is nontoxic and not associated with immune response.

The coating deposited by ALD may be used to mask the taste of bitter drugs. In one embodiment of the present invention, a pharmaceutical substrate is coated with a taste-improving agent, typically a sweetener, such as xylitol or sorbitol or their mixture. The coating problems previously associated with sweeteners, such a long coating times and moisture sensitive sweetener material can be overcome with the present method. Typical sweetener or other small molecule can be mixed with other chemicals according to the ALD coating procedure.

Precursor chemistry, process parameters and used substrates define the coating material characteristics. The coating layer may alternatively comprise one or more of various types of inorganic, organic and hybrid organic-inorganic polymer materials. The inorganic materials include nitrides, carbides, oxides, metals, sulfides, fluorides, etc. Inorganic oxides include, for example, silicon oxide or zinc oxide, or material such as CaO, CuO, $Er_2O_3$, $La_2O$, $ZrO_2$, $HfO_2$, $Ta_2O_5$, $Nb_2O_5$, MgO, $SC_2O_3$, $Ga_2O_3$, ZnO, $Y_2O_3$ and $Yb_2O_3$ without limiting to these.

Also biomaterials, such as hydroxyapatite, polymers, sugar, nanolaminates etc. are possible materials to be deposited. ALD enables a vast array of material combinations. Molecular layer deposition makes possible the deposition of organic polymers and hybrid organic-inorganic polymers. For a review of ALD process and its exploitation we refer to Puurunen R. L. J., Appl. Phys 97 (2005), pp. 1-52. An overview of the surface chemistry for the MLD of organic and hybrid organic-inorganic polymers can be seen e.g. in George, S. M. et al, (2009), *ACC. Chem. Res.,* 42, pp. 498-508.

A coating layer in accordance with the present invention may have various thicknesses, depending upon the particular application. In the coating process usually a coating that is as thin as possible is desirable such that it will be sufficiently thick in order to have the desired properties. ALD layer thickness can also be used to control the release of pharmaceutical substance and consequently control the drug dissolution time. The layer thickness can be defined by ALD cycles. For example, one ALD cycle of TMA and water results 0.1 nm thick $Al_2O_3$ coating. In one embodiment of the present invention, wherein trimethyl aluminum $(CH_3)_3Al$ is used as a precursor, the thickness of the coating is within the range of 1 nm to 500 nm, more preferably in the range of 1 of 100 nm, most preferably from 5 to 15 run. However, the coating layer may have any thickness between 1 nm and 500 µm. The thickness of the coating layer depends on the pharmaceutical substance, pharmaceutical ingredients and the desired final dosage form.

The temperature used in the coating process depends on the substrate properties and on the chosen precursor chemistry. In most common ALD methods it is advantageous to use relatively high temperature, because it allows molecules to evaporate readily and a coating having a sufficiently good quality is obtained. In the present invention a coating layer is deposited over a pharmaceutical substrate and therefore heat degradation of the pharmaceutical substrate is to be avoided or reduced. For example, the melting point of ibuprofein is around 74-77° C., whereas the melting point of paracetamol is around 169-172° C. The coating temperature may be from room temperature (RT) up to 350° C. Preferably the temperature for pharmaceuticals is below 200° C. In general, the present invention utilizes relatively low temperature ranges in contrast to vapor deposition methods, which are conducted at much higher temperatures.

The present invention may utilize any suitable ALD reactor. In one embodiment of the present invention, a static particle bed reactor is used. In this type of a reactor the particles are stationary on the reactor surface and overall and uniform coverage of each particles is depending e.g. on effective aspect ratio that particles are forming. One of the main obstacles in coating pharmaceuticals or nanoparticles is their natural tendency for aggregation. Among several factors, aggregation of cohesive particles is dependent on flow conditions as well as the external energy that is transferred to the particles during processing. Therefore, pharmaceuticals in different reactor configurations will show diverse aggregation patterns. Processing an ALD coating of pharmaceutical substrates in a fluidized bed reactor is preferred. Fluidized bed reactors offer advantages like higher heat and mass-transfer co-efficients and easy scalability. In addition due to the superior level of solids mixing in a fluidized bed conformally coated individual pharmaceutical particles are obtained. Also roll-to-roll ALD reactors may be utilized in the context of the present invention for depositing thin films on flexible pharmaceutical substrates, such as for example on transdermal patches.

The ALD coating according to the present invention may be used to influence on the particle release to the environment. For example, a poorly soluble coating allows for sustained release. Such poorly soluble coatings are e.g. aluminum oxide and titanium oxide. The coating on the pharmaceutical substance may comprise a plurality of inorganic coating layers or organic layers, or a combination of inorganic and organic layers to modify drug release rate. The use of multiple coating layers may allow for an additional degree of control in elution of a pharmaceutical substance. A greater number of deposited layers increasingly hinders elution of the drug and allows customization of time release.

Different coating layers may be used to produce different pharmaceutical dosage forms, such as immediate release, controlled release, and/or combinations of both immediate and controlled release dosage forms. Controlled release dosage forms, may include particles or beads containing a drug or active agent, where the particles or beads are coated with a release-controlling polymer. Controlled release beads may comprise an inert core, coated with an inner drug-containing layer and an outer membrane layer controlling drug release from the inner layer. The inert core may be a sphere or bead of sugar, a hydrophilic cellulosic polymer, or a crosslinked hydrophilic synthetic polymer.

The ALD coating according to the present invention may also be a responsive coating. Such a coating has a component such as a nanoparticle, responsive polymer or molecule incorporated in the coating. A responsive coating is able to give an appropriate and predictable response to outside condition changes and thus can enhance the performance of the pharmaceutical substance.

A pharmaceutical dosage form is a form in which a pharmaceutical formulation is presented in the medicinal product package as supplied by the marketing authorization holder, manufacturer, or distributor. The key defining characteristics of the pharmaceutical dosage form are the state of matter, delivery method, release characteristics, and the administration site or route for which the product is formulated. Pharmaceutical dosage forms are a mixture of active drug components and nondrug components. Depending on the method of administration they come in several types. These are liquid dosage form, solid dosage form and semi-solid dosage forms. Solid dosage forms, such as tablets and capsules, are the most established and preferred administration route. In the present invention a dosage form may be any dosage form which utilizes solid pharmaceutical particles. Such a dosage form may be, in addition to tablets and capsules, suppository, vaginary, liquid preparations, transdermal patches (transdermal drug delivery), medical ointments and emulsions (topical drug delivery, wound dressings), injection (parental drug delivery) and pulmonary drug delivery, without limiting to them. These can be administrated via nasal, rectal, vaginal, ear, eye, parenteral, per oral drug delivery route, without limiting to them.

A tablet is usually a compressed preparation that contains active substance, fillers, disintegrants, lubricants, glidants, binders and compounds which ensure disintegration, disaggregation, dissolution of the tablet in the stomach and intestine.

In common tableting processes, the material which is to be tableted is deposited into a cavity and one or more punch members are then advanced into the cavity and brought into intimate contact with the material to be pressed, whereupon a compression force is applied.

Three basic compression methods are common in most tableting operations, i.e., the wet granulation method, the double-compression method (also known as dry granulation) and the direct compression method. In each of these methods, there are blending steps which can promote agglomeration of fine particles of the drug into larger.

In the wet granulation method, pre-weighed drug and one or more other ingredients, like a diluent, are blended. The blend is then mixed with a liquid such as water or ethanol which causes the particles to agglomerate into a damp mass. Sometimes the liquid contains a binder. The damp mass is screened to produce granules which are then dried. The dry granules are screened to produce granules of a predetermined size. Then, the granules are typically blended with a solid lubricant and possibly other ingredients. Lastly, the lubricated granules and any other extra-granular ingredients are compressed into a tablet, which may subsequently be coated.

The double-compression or dry granulation method has fewer steps than wet granulation and does not require contact with a liquid or drying, which makes it well suited for formulating water sensitive and heat sensitive drugs. In the double-compression method, the drug and other ingredients, such as a lubricant, are blended and then compressed in a first compression step. There are two conventional first compression techniques. One is roller compaction where the blend is fed between rollers which press it into sheets and the other is slugging where the blend is compressed into slugs, which are tablet-like forms that are typically larger than tablets intended for human consumption. The resulting sheets or slugs are then comminuted into granules, mixed with a solid lubricant and compressed in a second compression step to produce the final tablet.

The direct compression method is the simplest of the three well known methods for making compressed solid dosage forms. In the direct compression method, the drug and any other ingredients are blended together and directly compressed into the final tablet. For various reasons, however, not all components which can be employed for the formulation of tablets are suitable for use in this process due to poor compressibility, flowability and stability under conventional tableting conditions.

The present invention relates to a procedure for preparing a pharmaceutical formulation and to a pharmaceutical formulation obtained by the process. In accordance with the present invention the pharmaceutical substrates are first coated by ALD after which all of the components, i.e., the coated active pharmaceutical substance, optionally any additional excipient(s) and other ingredient(s), are mixed together and processed into the final pharmaceutical dosage form. The final dosage form may be any dosage form which utilizes solid pharmaceutical particles. The present invention allows compression of the pharmaceutical substances directly after coating. In accordance with the present invention it is also possible to first coat the pharmaceutical substance and the excipient together and then proceed in manufacturing the dosage form. Alternatively, the excipient may be coated alone before making the pharmaceutical formulation.

The ingredients in the pharmaceutical formulation are mixed together using techniques well known in the art until the mixture is homogenous with respect to the drug. It is important that all ingredients are fairly dry, powdered or granular, somewhat uniform in particle size, and freely flowing. The pharmaceutical particles may be reduced in a particle size using conventional milling techniques, such as air jet milling, ball milling, cad milling, multi milling and other suitable size reduction techniques.

In a preferred embodiment the processing into the final dosage form is done by compressing. The term "compressing" includes any known process performed by applying compression forces. These methods include, but are not limited to, compression, compaction, extrusion and injection molding.

In one embodiment of the present invention the pharmaceutical dosage form is a tablet. Some active pharmaceutical agents may be tableted as pure substances, but this is rarely the case; most formulations include excipients, which are pharmacologically inactive ingredients added to help holding the tablet together and giving it strength. The pharmaceutically acceptable excipients may be selected from the group of diluents, surfactants, antioxidants, disintegrants, binders, lubricants, glidants, and chelating agents. Pharmaceutically accepted excipients are well known in the art and in this context we refer to e.g. Handbook of Pharmaceutical Excipients, 6th edition, Pharmaceutical Press and American Pharmacist's Association by Ray C. Rowe, Paul J. Sheskey and Marian Quinn. It should be noted that a tablet obtained by the method of the present invention may be further coated after being pressed to get for example a sugar-coated tablet or a film-coated tablet.

After making the final tableting blend for the pharmaceutical formulation, a lubrication step is used to ensure that the tableting blend does not stick to the equipment during the tableting process. This usually involves low shear blending of the pharmaceutical ingredients with a powdered lubricant, such as magnesium stearate or stearic acid.

Any conventional tablet presses, also called tableting machines, may be used from a hand-operated press or a single station tableting press to a multi-station rotary press. The operation of such machinery is well within the ordinary skill in the art.

The present invention relates also to a pharmaceutical formulation, wherein the pharmaceutical substrate is distributed as particles, and wherein the coating layer is deposited by ALD and the coating layer conformally coats over the individual particles of the pharmaceutical substrate. In one embodiment of the invention, the pharmaceutical formulation is in a dosage form which utilizes solid pharmaceutical particles, preferably it is a tablet.

The present invention also relates to the use of the ALD method or other corresponding technology for coating a pharmaceutical substrate.

It will be obvious to a person skilled in the art that as the technology advances, the inventive concept can be implemented in various ways. The invention and its embodiments are not limited to the examples described below but may vary within the scope of the claims.

EXAMPLES

Example 1. Pharmaceutical Substrate Coating

Pharmaceutical particles (as shown in Table 1) were coated by Beneq TFS 500 ALD tool, equipped with static particle bed reactor. This type of particle reactor is suitable for small amount of particles. The reactor is built up from five cells top of each other. Each cell is 200 mm of its diameter and 20 mm of its height. Paracetamol powder was loaded on the bottom of the reactor cells without any pretreatment and the reactor cells were then loaded into the reactor and pumped down to the operating pressure of around 2 mbar. $Al_2O_3$ and $TiO_2$ were deposited on paracetamol particles with average particle size of approximately 50 μm at temperature of 100 to 140° C. $Al_2O_3$ films were grown from trimethylaluminum (TMA) and water vaporized from the source at a temperature of 20° C. $TiO_2$ films were grown from tetrakis(dimethylamido)titanium (TDMAT) vaporized from the source at a temperature of 41° C. and water vaporized from the source at a temperature of 20° C. One deposition cycle for $Al_2O_3$ consisted of a 2 seconds metal precursor (TMA) pulse, 2.5 seconds $N_2$ purge, 0.5 second water pulse and 1 second $N_2$ purge. Similarly the timing sequence used for $TiO_2$ deposition was 1-5-1.5-2 seconds. The number of ALD cycles deposited for both oxides was 500.

Paracetamol (USP) was purchased from Hawkins Inc. (Hawkins Inc., MN, USA), mannitol was purchased from Roquette Freres, Lestrem, France, D-sorbitol from Sigma Aldrich and xylitol was commercial foodstuff.

Example 2. Tableting Study

The material obtained from Example 1 was tableted using an instrumented eccentric tableting machine (Korsch EK-0, Erweka Apparatebau, Heusenstamm, Germany) Flat-faced 9 mm punches were used and the die wall was lubricated using 5% (W/V) magnesium stearate in acetone before each compression. The target weights of tablets were 300 mg. Compression forces during the compression process were measured and the crushing strength of each tablet was measured using Scleuninger-E apparatus (Switzerland) (Table 1).

TABLE 1

Compression forces and the crushing strength of the resulting tablets

| Material | Upper punch force (kN) | Crushing strength (N) |
| --- | --- | --- |
| Neat paracetamol * | 8 kN | No tablet, no measurable crushing strength |
| Paracetamol + $Al_2O_3$ coating | 3.6 kN | 62N |
| Paracetamol + $TiO_2$ coating | 8.7 kN | 10N |
| Paracetamol + Xylitol 50%/Sorbitol coating 50% (w/w) [a] | 7.4 kN | 5N |

* no coating
[a] amorphous blend deposited using ALD equipment

The results presented in Table 1 show that flowability and processabiiity of the ALD coated pharmaceuticals is better than in pure paracetamol.

The invention claimed is:

1. A composition comprising individual nanoparticles or microparticles consisting of:
    i) an active pharmaceutical substance and a coating layer; or
    ii) an active pharmaceutical substance, one or more pharmaceutically acceptable excipients and a coating layer;
    wherein the coating layer is conformal, pinhole-free and consists of an inorganic oxide selected from the group consisting of aluminum oxide, zinc oxide, silicon oxide and titanium oxide, wherein the coating layer is applied by atomic layer deposition and is 5 nm-15 nm thick.

2. The composition of claim 1, wherein the individual nanoparticles or microparticles consist of an active pharmaceutical substance, at least one pharmaceutically acceptable excipient and a coating layer.

3. The composition of claim 1, wherein the individual nanoparticles or microparticles consist of an active pharmaceutical substance and a coating layer.

4. A pharmaceutical dosage form comprising the composition of claim 1 and a pharmaceutically acceptable carrier or excipient.

5. The pharmaceutical dosage form of claim 4 which is a liquid dosage form.

6. The pharmaceutical dosage form of claim 4 which is a solid dosage form.

7. The pharmaceutical dosage form of claim 4 which is a semi-solid dosage form.

8. The pharmaceutical dosage form of claim 4 which is an oral dosage form.

9. The pharmaceutical dosage of claim 4 which is a parenteral dosage form.

10. The composition of claim 1, wherein the active pharmaceutical substance is water soluble.

11. A composition comprising individual nanoparticles or microparticles consisting of:
    i) a water soluble active pharmaceutical substance and a coating layer; or
    ii) a water soluble active pharmaceutical substance, one or more pharmaceutically acceptable excipients and a coating layer;
    wherein the coating layer is conformal, pinhole-free and consists of an inorganic oxide selected from the group consisting of aluminum oxide, zinc oxide, silicon oxide and titanium oxide, wherein the coating layer is applied by atomic layer deposition and the total thickness of the coating layer is 1 nm-100 nm.

12. The composition of claim 11, wherein the individual nanoparticles or microparticles consist of an active pharmaceutical substance, at least one pharmaceutically acceptable excipient and a coating layer.

13. The composition of claim 11, wherein the individual nanoparticles or microparticles consist of an active pharmaceutical substance and a coating layer.

14. The composition of claim 11, wherein coating layer is 5 nm-15 nm thick.

15. A pharmaceutical dosage form comprising the composition of claim 11 and a pharmaceutically acceptable carrier or excipient.

16. A pharmaceutical dosage form comprising the composition of claim 2 and a pharmaceutically acceptable carrier or excipient.

17. The pharmaceutical dosage form of claim 16, wherein the active pharmaceutical substance is water soluble.

18. A pharmaceutical dosage form comprising the composition of claim 3 and a pharmaceutically acceptable carrier or excipient.

19. The pharmaceutical dosage form of claim 18, wherein the active pharmaceutical substance is water soluble.

20. A pharmaceutical dosage form comprising the composition of claim 12 and a pharmaceutically acceptable carrier or excipient.

21. The pharmaceutical dosage form of claim 20, wherein the coating layer is 5 nm-15 nm thick.

22. A pharmaceutical dosage form comprising the composition of claim 13 and a pharmaceutically acceptable carrier or excipient.

23. The pharmaceutical dosage form of claim 22, wherein the coating layer is 5 nm-15 nm thick.

* * * * *

UNITED STATES PATENT AND TRADEMARK OFFICE
CERTIFICATE OF CORRECTION

| | | |
|---|---|---|
| PATENT NO. | : 11,672,764 B2 | Page 1 of 1 |
| APPLICATION NO. | : 16/806625 | |
| DATED | : June 13, 2023 | |
| INVENTOR(S) | : Pekka Hoppu et al. | |

It is certified that error appears in the above-identified patent and that said Letters Patent is hereby corrected as shown below:

In the Specification

Delete "continuation" and insert -- divisional -- on Column 1 Line 9.

Signed and Sealed this
Eighth Day of August, 2023

Katherine Kelly Vidal
*Director of the United States Patent and Trademark Office*